United States Patent [19]

Klingenstein

[11] Patent Number: 5,700,252
[45] Date of Patent: Dec. 23, 1997

[54] LUMEN-SEEKING NASOGASTRIC TUBE AND METHOD

[76] Inventor: Ralph James Klingenstein, 151 Tremont St., Apt. 23E,, Boston, Mass. 02111

[21] Appl. No.: 551,453

[22] Filed: Nov. 1, 1995

[51] Int. Cl.$^6$ ............................................. A61M 25/00
[52] U.S. Cl. ..................... 604/280; 604/264; 604/49; 606/196
[58] Field of Search ................... 604/280, 264, 604/282, 53, 49, 54, 196

[56] References Cited

U.S. PATENT DOCUMENTS

| | | | |
|---|---|---|---|
| 2,211,975 | 8/1940 | Hendrickson | 128/349 |
| 2,268,321 | 12/1941 | Flynn | 128/349 |
| 4,385,635 | 5/1983 | Ruiz | 128/658 |
| 4,402,684 | 9/1983 | Jessup | 604/264 |
| 4,516,970 | 5/1985 | Kaufman et al. | 604/270 |
| 4,559,046 | 12/1985 | Groshong et al. | 604/282 |
| 4,563,181 | 1/1986 | Wijayarathna et al. | 604/280 |
| 4,594,074 | 6/1986 | Andersen et al. | 604/270 |
| 4,735,607 | 4/1988 | Keith, Jr. | 604/54 |
| 4,863,442 | 9/1989 | DeMello et al. | 604/282 |
| 4,886,067 | 12/1989 | Palermo | 128/657 |
| 4,886,506 | 12/1989 | Lovgren et al. | 604/280 |
| 4,888,146 | 12/1989 | Dandeneau | 264/171 |
| 4,957,110 | 9/1990 | Vogel et al. | 128/642 |
| 4,985,022 | 1/1991 | Fearnot et al. | 604/282 |
| 5,017,193 | 5/1991 | Fields | 604/270 |
| 5,078,702 | 1/1992 | Pomeranz | 604/280 |
| 5,100,385 | 3/1992 | Bromander | 604/99 |
| 5,383,852 | 1/1995 | Stevens-Wright | 604/95 |
| 5,560,747 | 10/1996 | McCue et al. | 606/196 |

FOREIGN PATENT DOCUMENTS

| | | |
|---|---|---|
| 0 191 471 A1 | 8/1986 | European Pat. Off. . |
| 0380873B1 | 5/1994 | European Pat. Off. . |
| 2 606 285 | 5/1988 | France . |
| 3034835A1 | 2/1982 | Germany . |
| 3286779A | 12/1991 | Japan . |
| 1559825 | 1/1980 | United Kingdom . |

OTHER PUBLICATIONS

Thomas J. Lardner et al., "An Introduction To The Mechanics of Solids", Second Edition (McGraw-Hill, Inc.) (1978), 582–590 and 595–596.

Counterpart PCT International Application No. PCT/US96/17496 IPEA Search Report (actual completion date 26 Feb. 1997).

*Primary Examiner*—John D. Yasko
*Attorney, Agent, or Firm*—Testa, Hurwitz & Thibeault, LLP

[57] ABSTRACT

Disclosed is an improved nasogastric tube having a coupled or integrally formed flexible tip which facilitates insertion and advancement of the tube through a nasopharynx and into a stomach of a patient while reducing the risk of trauma to the nasal cavity and perforation of the esophagus and other soft tissue. Geometry and material of the tip and tube body are selected so that the tip preferentially buckles before the tube body upon meeting body structure during advancement of the tube. Buckling of the tip passively steers the tip and tube body through the nasal cavity along the esophageal lumen, unlike conventional nasogastric tubes which tend to displace or perforate proximate body structure. Tip geometries include those which are cylindrical, frustoconical, tapered, bulbous, pleated and necked. Tips may be hollow or solid, symmetrical or asymmetrical, and may include a reinforcement member to modify the column strength thereof. One or more transition zones may be provided to transition between tube structures having differing column strengths.

23 Claims, 4 Drawing Sheets

 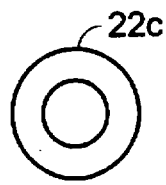
FIG. 5A　　　　　　　FIG. 5B
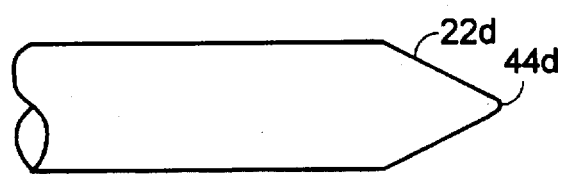 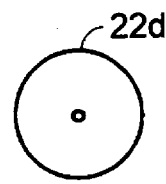
FIG. 6AA　　　　　　FIG. 6AB
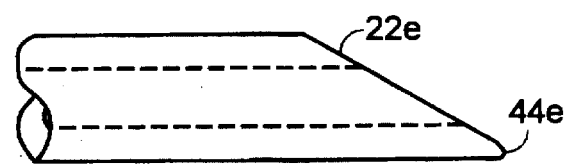 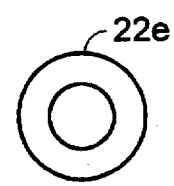
FIG. 6BA　　　　　　FIG. 6BB
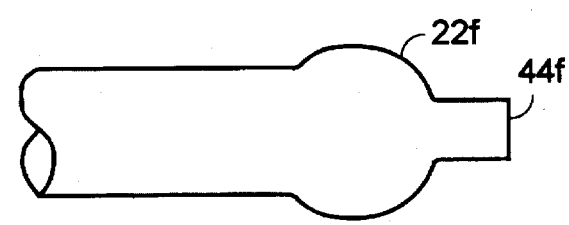 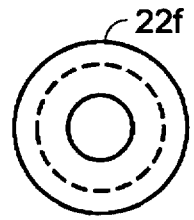
FIG. 7AA　　　　　　FIG. 7AB
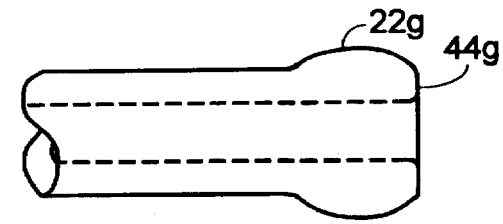 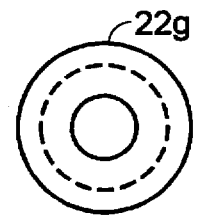
FIG. 7BA　　　　　　FIG. 7BB

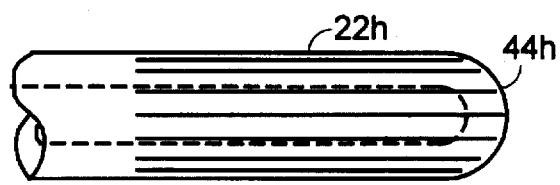
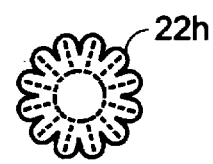
FIG. 8A  FIG. 8B
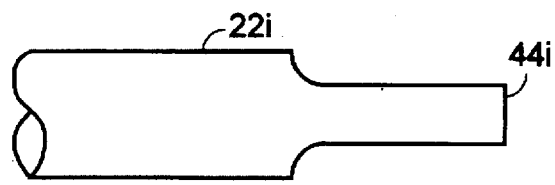
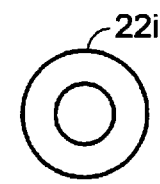
FIG. 9AA  FIG. 9AB
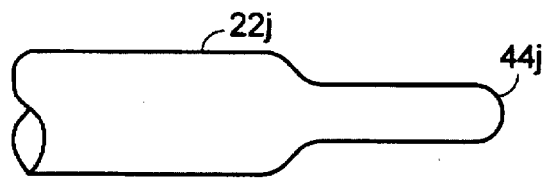
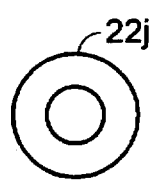
FIG. 9BA  FIG. 9BB
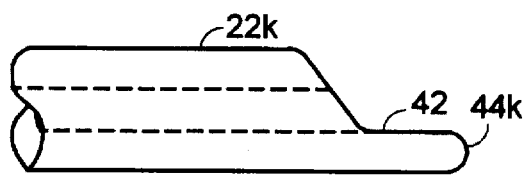
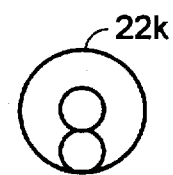
FIG. 9CA  FIG. 9CB
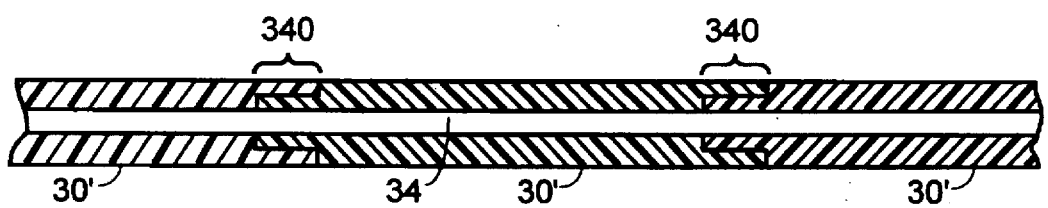
FIG. 10

LUMEN-SEEKING NASOGASTRIC TUBE AND METHOD

TECHNICAL FIELD

The present invention relates generally to tubes used for providing fluidic communication with an upper digestive system of a patient and more particularly to an improved nasogastric tube having a modified tip which facilitates insertion of the tube into a stomach or small intestine of a patient via a nasal cavity.

BACKGROUND INFORMATION

Nasogastric tubes are widely used for patient care to provide a means for removing gastric and other fluids from a patient's stomach or upper small intestine. Once inserted, such tubes can also be used for administering fluids such as medicines or nutritional supplements, although specialized feeding tubes have been developed for this purpose. A conventional nasogastric tube may be manufactured from a clear, elastically flexible polymer having a closed, rounded distal end portion or tip. The tube may have a single bore or lumen; however, a popular design employs a centrally disposed septum to subdivide the tube lumen into a suction lumen and a vent lumen. Fluidic communication between at least one lumen and the patient's stomach is provided by one or more apertures transecting a sidewall of the tube proximate the tip.

A nasogastric tube is conventionally inserted by placing a lubricated tip of the tube into a nostril of the patient and slowly advancing the tube by pushing on the exposed portion thereof. The tube must be sufficiently flexible to negotiate the tortuous, near 180 degree curvature of the nasopharynx, while sufficiently stiff to pass reliably through the hypopharynx and esophagus and into the stomach or small intestine. Insertion of the tube generally results in discomfort to the patient and often causes pain, nose bleeds or other trauma to the nasal cavity. In patients having an abnormality in platelet or coagulation function, such nasal cavity trauma can be particularly troublesome.

Once in the hypopharynx, the tip of the tube is carefully advanced into the esophagus to avoid intubating the patient's larynx. Caution must be exercised throughout advancement of the tube, as the tip of the tube is sufficiently stiff to perforate the wall of the esophagus and enter the mediastinum, requiring immediate recognition and treatment to prevent serious harm to the patient. The tube is advanced a predetermined amount, typically measured by permanent, incremental markings along the tube, correlating to a target location in the patient's digestive system. Actual location of the tip may then be verified by any of a number of methods, including, for example, fluoroscopic inspection of a radiopaque marker on the tube or listening for bubbling in the stomach after injection of air down a lumen of the tube.

Once location of the tip of the tube is verified in the target location, suction may be applied to the lumen to remove fluids or trapped air for diagnostic or therapeutic purposes. Alternatively, a source of medication or nutrition can be coupled with the lumen to supply needed fluid or entrained matter directly to the digestive system, although such practices are uncommon, being generally restricted to emergency situations.

Once properly inserted, nasogastric tubes are routinely left in place over extended periods of time, such as days, even when needed only from time to time. Repeated insertion and removal of the tube is avoided, both due to the risk of harm to the patient, as well as the time and difficulty associated with insertion. Generally, the difficulty encountered during initial insertion and placement of the tube outweigh the continuing discomfort to the patient once the tube is in place.

Attempts to facilitate insertion of the tube, such as by bending the tip into a slight curvature to initially accommodate the curvature of the nasal passage, often prove fruitless. While conventional nasogastric tubes are manufactured from flexible polymeric materials which readily deform under manipulation, such deformation is elastic in nature. The tip regains its free-state, linear contour quickly upon release. If the tip were to be plastically deformed or originally manufactured such that it were to retain an induced curvature or set, passage through the nasopharynx may be facilitated; however, passage of the tip beyond the nasopharynx, into the hypopharynx and esophagus, would be rendered substantially more difficult if not altogether impractical.

The design of nasogastric tubes typically balances competing needs for a flexible apparatus which is able to negotiate the tortuous path to a patient's stomach via the nasal passage while maintaining sufficient structural integrity to prevent sidewall collapse and blockage of the lumen when suction is applied. Further, the suction lumen must be of sufficient cross-sectional area and the tube of relatively small external diameter to support adequate volumetric flow rates while minimizing discomfort to the patient. Yet further, the tube must be sufficiently stiff so as to be capable of reliable advancement when an exposed portion thereof is pushed upon. This stiffness, however, is problematic insofar as stiffer tubes expose the patient to increased risk of trauma of the nasal cavity and perforation of the esophagus or other soft tissue.

SUMMARY OF THE INVENTION

The improved nasogastric tube includes a tube body having a lumen formed by a sidewall, the body being manufactured of a material and configured in a predetermined manner to exhibit a first stiffness or column strength. The terms stiffness and column strength are used interchangeably herein, being commonly defined as resistance to buckling when subjected to a substantially centrally disposed, longitudinal load. The greater the stiffness or column strength, the greater the critical load which can be stably supported by the element, and beyond which the element buckles or collapses.

Coupled with a distal end portion of the tube body along a transition zone is a tip configured to provide a second stiffness or column strength, the second column strength being less than the first column strength such that the tip collapses at a lower critical load. During insertion of the tube through the nasopharynx and upper digestive system of a patient, upon encountering tissue, bone, cartilage or other body structure along the direction of advancement, the tip preferentially buckles before the tube to prevent trauma to the nasal cavity or perforation of soft tissue. Further, given the physical contour of the nasopharynx and hypopharynx, as the tip buckles, the tip and tube body are passively oriented toward the body passage lumen, unlike conventional nasogastric tubes which tend to displace or perforate or otherwise traumatize body structure.

The tip may be manufactured from a relatively soft, flexible material which bends or buckles toward the body passage lumen upon advancement against body structure.

Further, the resultant blunt tip is even less prone to cause trauma to or perforation of proximate body structure. The remainder of the tube may be manufactured of a relatively stiff material. During insertion, the more compliant tip reduces the likelihood of discomfort and trauma by providing a lumen-seeking function, bending or collapsing upon encountering body structure and passively steering the nasogastric tube through the nasal passage, along the esophagus and into the stomach. Any deviation in travel from the centerline of the esophageal lumen during advancement of the tip is automatically passively corrected.

The tip mates with the tube body along a transition zone using a bonded male/female connection which will generally exhibit a third stiffness or column strength. Depending on the particular configuration employed, the transition zone stiffness may be advantageously tailored to be greater than that of the tip and less than that of the tube body thereby providing an intermediate transitional stiffness to further facilitate the lumen-seeking function of the tube.

The tube may advantageously include a coiled wire reinforcement member which is either embedded in the tip or surrounds the tip, being anchored in the transition zone. The reinforcement member may be primarily employed to modify the stiffness of the tip, for example to enhance resistance to buckling while permitting controlled bending of the tip once buckling occurs. The wire member may also act as a fail-safe, preventing release of the tip in a patient's body in the event of inadvertent failure of the connection between the tip and the tube body.

Alternately, the tip may be manufactured from the same material as the tube body and may advantageously be formed integrally with the tube body, especially where a hollow tip is desired. In this embodiment, column strength may be tailored by modifying the geometry of the tip to reduce the moment of inertia and related critical buckling load thereof relative to those of the tube body. In this manner, preferential buckling of the tip may be achieved in a tube having unitary construction. Further, instead of having uniform column strength, the tip and/or tube may exhibit incrementally or gradually varying column strength as desired. For example, column strength may be varied to provide for increasing stiffness as a function of distance from the end of the tip. In tubes with either integral or bonded tips, the tips may be solid or hollow; cylindrical, frustoconical, tapered, bulbous, pleated or necked; symmetrical or asymmetrical; and may include one or more apertures in fluid communication with the lumen of the tube.

BRIEF DESCRIPTION OF THE DRAWINGS

The invention in accordance with preferred and exemplary embodiments, together with further advantages thereof, is more particularly described in the following detailed description taken in conjunction with the accompanying drawings in which:

FIGS. 5A–5B are schematic, plan and end views of a frustoconical tip configuration in accordance with a preferred embodiment of the present invention;

FIGS. 6AA–6BB are schematic, plan and end views of two tapered tip configurations in accordance with other preferred and exemplary embodiments of the present invention;

FIGS. 7AA–7BB are schematic, plan and end views of two bulbous tip configurations in accordance with various embodiments of the present invention;

FIGS. 8A–8B are schematic, plan and end views of a pleated tip configuration in accordance with one embodiment of the present invention;

FIGS. 9AA–9CB are schematic, plan and end views of three necked tip configurations in accordance with various embodiments of the present invention; and FIG. 10 is a schematic, longitudinal sectional view of the tube body depicted in FIG. 2A, generally in accordance with an alternate embodiment of the present invention.

MODE(S) FOR CARRYING OUT THE INVENTION

Figure 1:
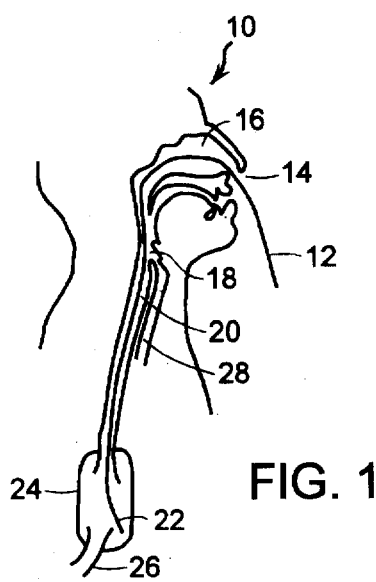
FIG. 1 is a schematic, partial cutaway side view of a patient fitted with a nasogastric tube in accordance with a preferred embodiment of the present invention.

Depicted in FIG. 1 is a schematic, partial cutaway side view of an upper torso and cranium of a patient 10 fitted with a flexible, substantially cylindrical nasogastric tube 12 in accordance with an exemplary embodiment of the present invention. The tube 12 passes serially through nostril 14, nasopharynx 16, hypopharynx 18, and esophagus 20 with tube tip 22 terminating in stomach 24. Alternatively, the tube 12 may be advanced further so that the tip 22 is disposed in an upper portion of the small intestine 26, although in practice, such procedures entail additional difficulty. Care is exercised during advancement of the tube 12 to prevent trauma to the nasopharynx 16, intubation of the larynx 28 and/or perforation of the esophagus 20.

Figure 2A:
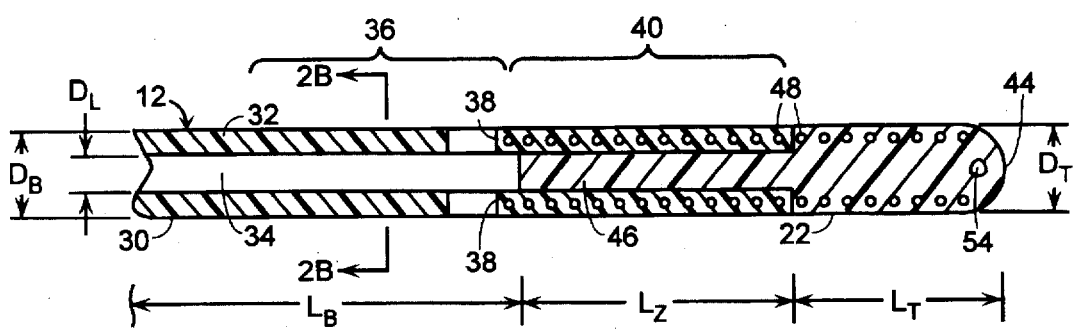
FIG. 2A is a schematic, longitudinal sectional view of the tube body distal end portion and tip depicted in FIG. 1, generally in accordance with a preferred embodiment of the present invention.

As best seen in FIG. 2A, the tube 12 includes a substantially cylindrical, flexible tube body 30 formed by a sidewall 32 which defines a centrally disposed, longitudinally extending bore or lumen 34. A distal end portion 36 of tube body 30 includes at least one aperture 38 transecting the sidewall 32 to provide fluidic communication between the lumen 34 and an environment in which the end portion 36 is disposed. Two diametrically opposed apertures 38 are depicted; however, the number, size, location, shape, and orientation of the apertures 38 may be selected in accordance with conventional practice by those skilled in the art of nasogastric tube design.

Figure 4A:
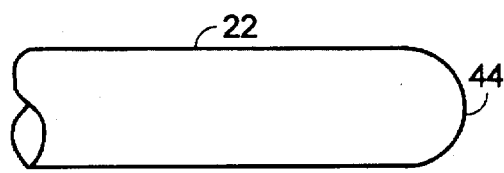
FIGS. 4AA–4CB are schematic, plan and end views of three cylindrical tip configurations in accordance with various embodiments of the present invention.
Figure 4A:
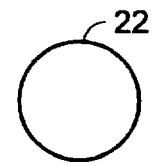

Coupled with the end portion 36 along a transition zone 40 is a substantially cylindrical, flexible tip 22 having a smooth, generally spherical end 44. Tip 22 and numerous alternate tip configurations are depicted in FIGS. 4AA–9CB inclusive. It is contemplated that a gently tapered tip configuration, such as that depicted in FIG. 6AA, is preferred; however, tip 22 may be considered representative for purposes of explanation.

Reliable coupling of the tip 22 to the distal end 36 is afforded by inserting a centrally disposed, longitudinally extending leader 46 of the tip 22 into the lumen 34. The leader 46 may be sized to match a nominal diameter of the lumen 34 or preferably may be an interference fit therewith. The leader 46 and lumen 34 together form a male/female connection which may be bonded, friction welded or otherwise permanently coupled along mating surfaces thereby forming an inseparable assembly. The manner of coupling may be selected in accordance with conventional practice for the materials chosen for the respective elements. As depicted herein, the length of the tip 22, $L_T$, is substantially equal to the length of the transition zone 40, $L_Z$, although values may be selected to achieve desired respective column strengths as will be discussed in more detail hereinbelow. Alternatively, the tip 22 may be molded or otherwise formed in place along the distal end 36.

In either embodiment, a coiled wire reinforcement member 48 may be advantageously embedded or anchored in both the tip 22 and sidewall 32. As will be discussed in greater detail hereinbelow, the reinforcement member 48 may be employed to modify the stiffness of the tip 22 and transition zone 40 to achieve desired resistance to buckling through selection of coil diameter and pitch values. Additionally, in the event the coupling between the tip 22 and distal end 36 fails during manipulation of the tube 12 in a patient 10, the tip 22 is retained and may be readily extracted along with the tube 12. Wire diameter and material may be selected to provide sufficient structural integrity for anticipated extraction loads.

By coupling the tip 22 to the distal end 36 in any of the manners described, the tube 12 exhibits a uniform, smoothly contoured external configuration without steps, ridges or other local discontinuities which would tend to render insertion and removal of the tube 12 in a patient 10 more difficult. Respective outer diameters of the tip, $D_T$, and the tube body, $D_B$, have similar values which are substantially constant along respective lengths thereof; however, such values may vary as a function of position to vary stiffness as will be discussed in greater detail hereinbelow.

The transition zone 40 functions to transition between the stiffness and geometry of the tip 22 and those of the tube body 30. As will be discussed with respect to FIG. 10, the tube body 30 may also incorporate additional body transition zones 140 to transition between sections of tube body 30' having differing respective column strengths and/or geometries, further facilitating the lumen-seeking function of the tube 12.

Figure 2B:
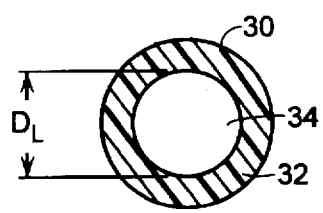
FIG. 2B is an enlarged schematic, cross-sectional view of the tube body of FIG. 2A taken along line 2B—2B in accordance with a preferred embodiment of the present invention.
Figure 2C:
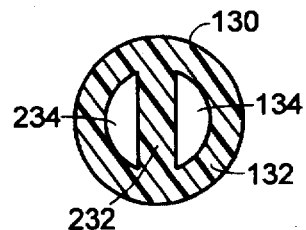
FIG. 2C is an enlarged schematic, cross-sectional view of a tube body in accordance with another embodiment of the present invention.

FIG. 2B is an enlarged schematic, cross-sectional view of the tube body 30 of FIG. 2A taken along line 2B—2B. Solely a single lumen 34 is defined by the sidewall 32, the diameter of which is designated $D_L$. FIG. 2C depicts a similar view of a tube body 130 having a suction lumen 134 and a vent lumen 234 defined by sidewall 132 and a generally diametrically disposed septum wall 232. Clearly, more than one septum 232 may be provided to further subdivide each lumen 134, 234 and placement of the septa may yield lumens of different cross-sectional contour and area, as desired.

Column strength of an element, defined herein as resistance of the element to buckling, is a function of a variety of factors including the geometry and material properties of the element as well as the end conditions to which the element is subjected. Taking the tube 12 of FIG. 2A as an example, the configuration of each section of the tube 12 may be modeled to develop a critical load, $P_{CRIT}$, below which that section of the tube 12 is structurally stable. Above $P_{CRIT}$, that section of the tube 12 is unable to support the load and the section will buckle.

Analytically, for a column subjected to a centrally-disposed, longitudinal load, elastic buckling occurs at loads greater than $P_{CRIT}$, with $P_{CRIT}$ being defined as:

$$P_{CRIT} = cEI/L^2 \qquad (1)$$

where E is the modulus of elasticity of the column material, I is the moment of inertia of the column about its longitudinal axis, L is the unsupported length of the column and c is a factor employed to account for end conditions. Conventionally modeled column end conditions include, for example, various combinations of free, clamped and hinged configurations. Given the physical constraints on the tube 12 as it is inserted and advanced in a patient's body, the end conditions may be modeled as a clamped-free column. Substituting the associated value of $\pi^2/4$ for c for a clamped-free column in critical load equation (1) yields:

$$P_{CRIT} = \pi^2 EI/4L^2. \qquad (2)$$

Regarding tube 12, the tube body 30 may be modeled a hollow circular cylinder, the transition zone 40 as a solid, circular cylinder and the tip 22 as another solid, circular cylinder. Subscript "$_T$" refers to the tip 22 subscript "$_B$" to the body 30, subscript "$_L$" to the lumen 34 and subscript "$_Z$" to the transition zone 40.

Looking first to the tip 22, the moment of inertia of the solid, circular, cylindrical tip, $I_T$, may be defined as:

$$I_T = \pi m_T L_T D_T^4/32 \qquad (3)$$

where $m_T$ is the mass per unit volume of the tip, $L_T$ is the length of the tip and $D_T$ is the outer diameter of the tip as shown in FIG. 2A. Substituting moment of inertia equation (3) for I in critical load equation (2) yields:

$$P_{TCRIT} = \pi^3 m_T E_T D_T^4/128 L_T. \qquad (4)$$

To calculate the critical tube body load, $P_{BCRIT}$, the tube body 30 has a moment of inertia, $I_B$, defined as that for a hollow circular cylinder:

$$I_B = \pi m_B L_B (D_B^4 - D_L^4)/32 \qquad (5)$$

where $m_B$ is the mass per unit volume of the body, $L_B$ is the unsupported length of the body, $D_B$ is the outer diameter of the body and $D_L$ is the diameter of the lumen as shown in FIG. 2A. Substituting into critical load equation (2) yields:

$$P_{BCRIT} = \pi^3 m_B E_B (D_B^4 - D_L^4)/128 L_B. \qquad (6)$$

Lastly, the critical load for the solid, circular cylinder transition zone 40 may be defined by:

$$P_{ZCRIT} = \pi^3 m_Z E_Z D_Z^4/128 L_Z \qquad (7)$$

where the modulus of elasticity of the transition zone 40, $E_Z$, is a combination of the moduli of the tip 22 and the body 30 and which may be conventionally analytically or empirically determined. For the configuration of tube 12 depicted in FIG. 2A, $P_{ZCRIT}$ will necessarily be greater than $P_{BCRIT}$ and therefore need not be considered further. Other preferred embodiments of transition zone 40 are discussed hereinbelow with respect to FIGS. 2D and 2E in which the stiffness of the transition zone 40 may be intermediate between that of the tip 22 and tube body 30 or in which the transition zone 40 includes a plurality of transition zones of graded stiffness.

Clearly, a designer may select any desired combination of materials and geometries to satisfy the requirement that the tip 22 preferentially buckle before the tube body 30, expressed in equation form as:

$$P_{TCRIT} < P_{BCRIT} \qquad (8)$$

In this manner, the lumen-seeking capability of the tube is enabled.

While this analytical modeling does not account for features such as apertures 38 through the tube body sidewall 32, the inclusion of such features in the tube body 30, for example, will tend to reduce the resultant resistance to buckling and the critical load, $P_{BCRIT}$; therefore, sufficient margin should be provided in the design of any tube 12 to accommodate for such structural discontinuities. Generally, the greater the number, size and local density of the apertures 38, the greater the margin that should be provided. Given the analytical guidelines disclosed hereinabove, a tube 12 may be readily designed by those skilled in the art without undue experimentation. Further, since manufacture and testing of contemplated combinations of materials and geometries to verify preferential buckling may be readily accomplished at modest cost, empirical results may be used to guide modification and tailoring of the tube 12 for particular aperture patterns and combinations which would otherwise entail more complex analytical modeling.

Where, as in tube 12, the outer diameters of both the tube body 30 and tip 22 are equivalent and constant, substituting respective tip and tube body critical load equations (4) and (6) into preferential buckling equation (8) and simplifying yields:

$$m_T E_T / L_T < m_B E_B (1 - D_L^4 / D_B^4) / L_B. \qquad (9)$$

A designer could meet the preferential buckling criteria of equation (9) in a variety of ways. For example, a designer could provide a tip 22 having a longitudinal length, $L_T$, greater than the anticipated unsupported longitudinal length of the body 30, $L_B$, during insertion of the tube 12 in a patient 10. Since tip critical buckling load, $P_{TCRIT}$, varies with the inverse of longitudinal length, an increase in tip length, $L_T$, reduces $P_{TCRIT}$. Alternately or additionally, $P_{TCRIT}$ may be reduced relative to $P_{BCRIT}$ by employing a tip material having relatively lower mass per unit volume, $m_T$, than body material mass per unit volume, $m_B$, and/or a tip material having a relatively lower modulus of elasticity $E_T$ than body modulus of elasticity $E_B$. Yet further, $P_{BCRIT}$ may be increased by increasing thickness of the sidewall 32 and thereby decreasing lumen diameter, $D_L$, in the tube body 30.

Figure 2D:
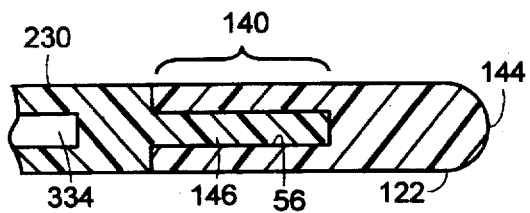
FIG. 2D is a schematic, longitudinal sectional view of the transition zone depicted in FIG. 2A in accordance with a preferred embodiment of the present invention.

FIG. 2D depicts a schematic, longitudinal sectional view of a transition zone 140 similar to that depicted in FIG. 2A in accordance with a preferred embodiment of the present invention. Instead of coupling the tip 22 to the tube body 30 by disposing tip leader 46 in tube lumen 34, tube body 230 includes a generally centrally disposed tube leader 146 disposed in a suitably sized bore 56 of tip 122. Tube lumen 334 is preferably truncated in advance of the transition zone 140; however, in an alternate embodiment, lumen 334 may pass therethrough. In accordance with the analytical model outlined hereinabove, materials and geometries may be selected such that the critical load of the transition zone 140, above which the zone 140 would buckle, is intermediate between that of the tip 122 and tube body 230. In this manner, the buckling strength of this overall configuration will generally incrementally increase as a function of distance from the end 144 of the tip 122. In other words, as loading is increased, the tip 122 would buckle first, the intermediate zone 140 would buckle next and the tube body 230 thereafter.

Figure 2E:
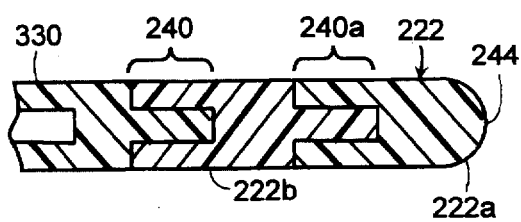
FIG. 2E is a schematic, longitudinal sectional view of the transition zone depicted in FIG. 2A in accordance with an alternate preferred embodiment of the present invention.

If additional tailoring of incremental buckling strength of the tip 122 is desired, additional tip transition zones 240a may be employed. For example, FIG. 2E depicts a schematic, longitudinal sectional view of multiple transition zones 240, 240a in accordance with an alternate preferred embodiment of the present invention, two such zones 240, 240a being depicted herein. Tip 222 is comprised of two members 222a, 222b which are coupled by a male/female connection along tip transition zone 240a, although any other suitable method of coupling, as described hereinabove, may be employed if desired. Tip member 222b is coupled to tube body 330 by similar means along transition zone 240. Again, by selecting materials and geometries in accordance with the analytical model, respective critical loads of serially arranged tip member 222a, tip transition zone 240a, tip member 222b, transition zone 240, and tube body 330 may be tailored to provide incrementally increasing resistance to buckling as a function of distance from end 244. Any number of tip transition zones 240a, and proximate tip members 222b may be employed to further refine and tailor buckling characteristics to achieve a desired result.

Figure 3:
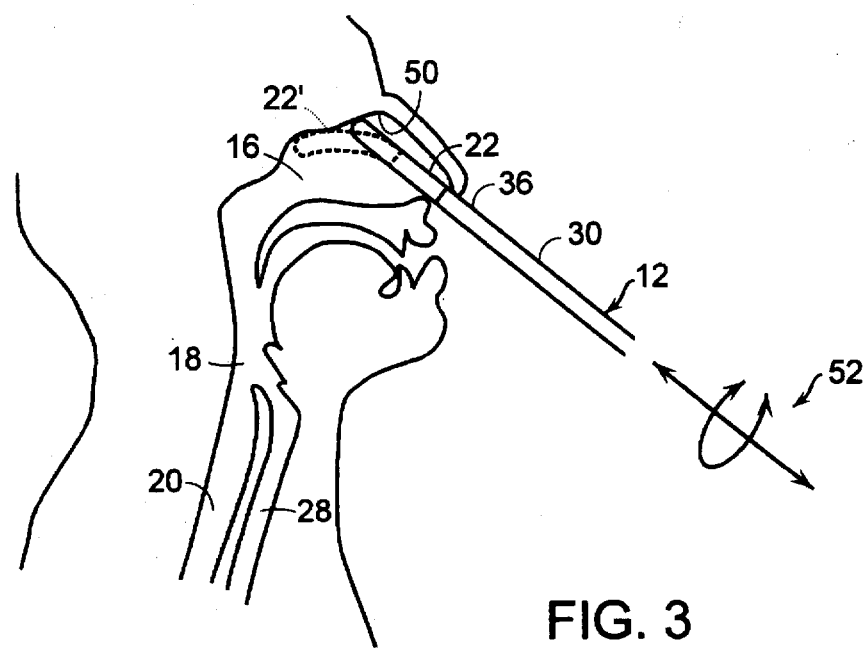
FIG. 3 is an enlarged, schematic partial cutaway view of a nasopharynx of a patient during insertion and advancement of the tube of FIG. 2A in accordance with an exemplary embodiment of the present invention.

Referring now to FIG. 3, depicted is an enlarged, schematic partial cutaway view of the nasopharynx 16 of the patient 10 depicted in FIG. 1 during insertion and advancement of the tube 12. In free state, the tube body 30 and tip 22 are substantially straight and collinear. Upon encountering body structure, such as nasal bone 50, continued advancement of the tube 12 causes buckling of the tip 22' as depicted in phantom. The tube body 30 retains structural integrity, remaining substantially straight, to facilitate manipulation of the exposed portion of the tube 12. As the tube is advanced further, the buckled tip 22' tends to reduce local pressure on the nasal bone 50 by increasing the surface area upon which the force applied to the tube 12 impinges. Further, the buckled tip 22' redirects the direction of the applied force generally along the direction of buckling, passively steering the distal end portion 30 toward the hypopharynx 18 and esophagus 20 as desired. As the tube 12 is advanced further, proximate tissue supports the tube body 30 permitting the tip 22 to regain its free state, linear configuration until other body structure is encountered.

In addition to merely subjecting the exposed portion of the tube 12 to a longitudinal advancing force, the tube 12 may be retracted or twisted, as depicted by the arrows shown generally at 52, to further direct the tip 22 and end portion 30 in a desired direction. Additionally, the tube 12 may be incrementally advanced and retracted repeatedly by a technique known as dithering. Such a technique may be employed advantageously when the tip 22 impinges upon body structure such as nasal bone 50 at an angle, as will almost always be the case. By dithering the exposed portion of the tube 12, the tip 22 will tend to alternately buckle and straighten, incrementally moving along the nasal bone 50 and through the nasopharynx 16 permitting the tube 12 to be advanced. Once in the hypopharynx 18, intubation of the larynx 28 by the tube 12 may be avoided by repeated swallowing by the patient 10 as is conventionally known. As the tube 12 is further advanced along the esophagus 20, any deviation in travel from the centerline of the esophageal lumen causes the tip 22 to buckle. Again, the buckled tip 22' both redirects the relatively stiff distal end 36 away from the esophageal wall, toward the esophageal lumen, and reduces pressure on the wall tissue, significantly reducing the likelihood and risk of perforation thereof. Once the end portion 36 has reached the target destination in the stomach 24, for example, and position is confirmed, suction may be applied to tube lumen 34 and fluids extracted conventionally.

The embodiment of the invention depicted in FIG. 2A provides a general purpose nasogastric tube designed for universal use. In an exemplary embodiment, tube body 30 and tip 22 may be manufactured from medical grade polyurethane or other polymer or material which may be sterilized and which is stable in a digestive system environment for extended periods. For a tube 12 having a tube body outer diameter, $D_B$, of about 6.0 mm, a nominal lumen diameter, $D_L$, of about 3.0 mm and an overall length of about 120 cm, the tip 22 may have a similar outer diameter, $D_T$, of about 6.0 mm and a length, $L_T$, of about 5.0 cm. The transition zone 40 may have a similar length, $L_Z$, of about 5.0 cm, more or less, with the tip leader 46 being inserted into the lumen 34 with a slight interference fit and coupled to the tube body 30 by bonding with an epoxy resin. As discussed hereinabove, sizing of the various elements of the tube 12 as well as the method of bonding depends upon the properties of selected material(s). If a coiled wire reinforcement member 48 is utilized, a preferred material is medical grade stainless steel.

The outer diameter of the tube body 30, commonly referred to by a measurement standard known as the French size which is about three times the diameter value in millimeters, may be increased or decreased as desired to accommodate patients of all body sizes; however, since the tube body critical buckling load does not vary linearly with lumen diameter, $D_L$, scaling may not be equally proportional for all tube features. For general purpose tubes 12, tube body diameter, $D_B$, will generally be in the range of about 6 Fr. to 18 Fr., corresponding to values of about 2 mm to about 6 mm; however smaller and larger diameter tubes 12 are considered to fall within the scope of the invention. Lumen diameter, $D_L$, may nominally be about one half the value of $D_B$ selected; however, values as low as about 10% or less or as high as about 90% or more of $D_B$ are possible, depending on the properties of the selected materials. Tip diameter, $D_T$, is nominally matched with body diameter, $D_B$; however, as will become apparent, various non-cylindrical tip configurations with respective diameters varying as a function of tip length are contemplated. Depending on the configuration selected, $D_T$ may range from values greater than $D_B$ to a value approaching zero. Tip length, $L_T$, may also vary from values of less than about 1 cm to values greater than about 10 cm or more. Tube body length, $L_B$, may be any value and transition zone length, $L_Z$, is generally the result of the coupling method employed between the tip 22 and tube body 30. Nominally the same as tip length, $L_T$, transition zone length, $L_Z$, may approach zero for those tubes 12 having tips 22 integrally formed with the tube body 30 to values greater than $L_T$ to ensure reliable coupling, as necessary.

In addition to scaling the size of the tube 12 to accommodate different patient body sizes, a designer has great leeway in varying relative column strengths. For example, soft, nominal and stiff tips 22 may be provided in each size tube 12 to be used at the discretion of the medical practitioner depending on the frailty of the patient 10. In all cases, the tip 22 preferentially buckles before the tube body 30.

The scope of the invention is not limited to the cylindrical tip configuration depicted in FIG. 2A. Insertion of a tube 12 in a patient 10 having particular characteristics may be facilitated where the tip 22 has an asymmetric or non-cylindrical tip configuration. For example, a patient having an anomalous nasal structure or a displaced esophageal lumen may benefit from a tube having a tip 22 with a reduced outer diameter, $D_T$, relative to that of the body 30. Further, since an asymmetric tip will generally have a tendency to buckle repeatably in the same direction, such a feature may be advantageously employed in particularly troublesome situations where symmetrical, non-directional tip configurations prove difficult to insert.

The remaining figures depict additional tip configurations which may be used depending, for example, on the age, infirmity or physical characteristics of a patient 10. Depending on the particular configuration, such tips 22 may be separate elements coupled to the tube body 30 in any manner described hereinabove. Alternatively, in those embodiments exhibiting sufficiently attenuated column strength, the tips 22 may be formed integrally with the tube body 30, obviating the bonded connection. The lumen 34 of the tube body 30 may be in fluidic communication with a hollow feature of the tip 22 or may be blocked by the tip 22, as desired. Further, any hollow feature of the tip 22 need not be in fluidic communication with the tube lumen 34, being employed primarily to tailor tip column strength.

Figure 4B:
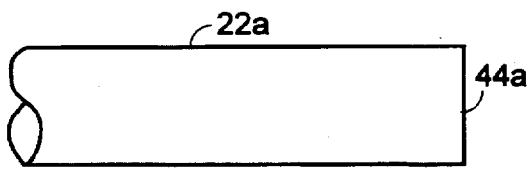
Figure 4B:
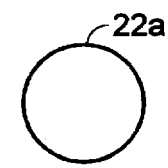
Figure 4C:
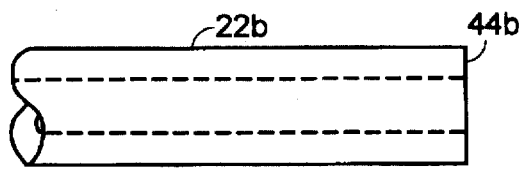
Figure 4C:
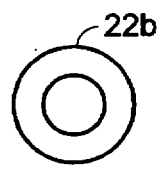

FIGS. 4AA-4CB are schematic, plan and end views of working ends of three cylindrical tip configurations in accordance with various embodiments of the present invention. FIGS. 4AA-4AB depict the solid, cylindrical tip 22 of tube 12 shown in FIG. 2A. The tip 22 has a uniform diameter, circular cross-section and generally spherical end 44. FIGS. 4BA-4BB an alternate embodiment solid, cylindrical tip 22a. The tip 22a has a uniform diameter, circular cross-section and generally truncated end 44a. FIGS. 4CA-4CB depict an alternate embodiment hollow, cylindrical tip 22b. The tip 22b has an annular cross-section with uniform inner and outer diameters and a generally truncated end 44b. Combinations of features depicted in these various embodiments are also contemplated. For example, tip 22 of FIGS. 4AA-4AB could be hollow.

FIGS. 5A-5B are schematic, plan and end views of a solid, frustoconical cylindrical tip 22c in accordance with another embodiment of the present invention. Tip 22c has a circular cross-section of decreasing area as a function of length and a generally truncated end 44c.

FIGS. 6AA-6BB are schematic, plan and end views of two tapered tip configurations in accordance with still further embodiments of the present invention. FIGS. 6AA-6AB depict a preferred embodiment solid, gently symmetrically tapered, conical tip 22d. Rate of taper or slope may be selected as desired. Tip 22d has a circular cross-section of gently decreasing area as a function of length and a generally blunt, radiused end 44d. FIGS. 6BA-6BB depict a hollow, asymmetrically tapered tip 22e. Tip 22e has an annular cross-section with decreasing cross-sectional area as a function of length and a generally blunt, radiused end 44e.

FIGS. 7AA-7BB are schematic, plan and end views of two bulbous tip configurations in accordance with additional embodiments of the present invention. FIGS. 7AA-7AB depict a solid, symmetrical bulbous tip 22f. Tip 22f has a circular cross-section of increasing then decreasing area as a function of length and an optional, generally blunt, truncated end 44f having a circular cross-section. FIGS. 7BA-7BB depict a hollow, symmetrical bulbous tip 22g. Tip 22g has an annular cross-section of increasing then decreasing area as a function of length and a generally blunt, truncated end 44g.

FIGS. 8A-8B are schematic, plan and end views of a hollow, pleated tip 22h in accordance with another embodiment of the present invention. Tip 22h has a multi-lobed cross-section of substantially constant area and a closed, generally spherical end 44h. When tip 22h buckles upon meeting body structure, the tip 22h may buckle asymmetrically, bending away from its longitudinal axis, or symmetrically, essentially shortening its overall length while the lobed sidewall expands radially outwardly. The mode of buckling may be influenced, for example, by varying the number and length of the pleats and the thickness of the sidewall.

Lastly, FIGS. 9AA-9CB are schematic, plan and end views of three necked tip configurations in accordance with further embodiments of the present invention. FIGS. 9AA-9AB depict a solid, symmetrical necked tip 22i. Tip 22i has a circular cross-section of rapidly decreasing then constant area as a function of length and a truncated end 44i having a circular cross-section. FIGS. 9BA-9BB depict a solid, symmetrical necked tip 22j. Tip 22j has an circular cross-section of gradually decreasing then constant area as a function of length and a spherical end 44j. FIGS. 9CA-9CB depict a hollow, asymmetrical necked tip 22k. Tip 22k has a generally annular cross-section with a solid extension 42 of circular cross-section longitudinally extending from a region of the annulus, the extension 42 having a spherical end 44k.

While there have been described herein what are to be considered exemplary and preferred embodiments of the present invention, other modifications of the invention will become apparent to those skilled in the art from the teachings herein. For example, various permutations of the tips 22 and ends 44 depicted may be employed to achieve a desired configuration to suit a particular application. Further, any of the tips 22 may be made hollow, fully or in part, to modify the column stiffness thereof or provide for fluidic extraction therethrough. Also, instead of being fully embedded within the sidewall 32 and tip 22, optional coiled wire reinforcement member 48 may be used to externally wrap at least a portion of the transition zone 40 and/or tip 22. Yet further, the coil 48 may be tightly or loosely wrapped and the pitch may vary as a function of longitudinal location to provide varying column strength along the tip 22. As may be readily appreciated, hollow tip wall thickness may also vary as a function of tip length to vary tip column strength. Configurations other than coils and materials other than wire may also be employed. For example, wire or plastic rings, or longitudinally disposed slivers of a desired material may be embedded in the tip 22. Instead of circular or annular cross-sections, tips 22 may have oval, contoured or polygonal cross-sections, with or without lumen 34 or aperture(s) 36. A lumen 34 of a tip 22 need not have the same diameter as the tube lumen 34 and any such tip lumen 34 need not have a circular cross-section. Multiple tip lumens 34 may also be provided, as desired. Asymmetric tips 22 may be advantageously employed where it is desirable for the tip 22 to buckle repeatably in a predetermined direction relative to the tube body 30.

Still other modifications are contemplated. For example, a tube 12 may be provided with a tip 22 which is relatively soft proximate the end 44 thereof and which exhibits increasing stiffness as a function of tip length as the transition zone is approached. The tube body 30 may also include a removable wire stiffener which is temporarily disposed in a lumen 34 and extends along substantially the entire length of the tube body 30, providing additional column strength to the tube body 30 during insertion and advancement. For this configuration, the calculation of body critical load, $P_{BCRIT}$, should include the effect of the stiffener. The tube body and/or tip may further include a radiopaque stripe, band or other marker to facilitate fluoroscopic verification of the location of the tube 12 in the body of a patient. An exemplary radiopaque marker 54 is depicted in the tip 22 in FIG. 2A.

Yet further, as depicted in FIG. 10, instead of solely a single transition zone 40, which is disposed between the tip 22 and tube body 30, the tube body 30 may include one or more additional body transition zones 340. The body transition zones 340 may be disposed along the length of the tube body 30 between tube body sections 30' having differing respective column strengths. In this manner, the tube body 30 may exhibit increasing stiffness, for example, as a function of distance from the tip 22, thereby facilitating the lumen-seeking capability of the tube 12. The multiple sections 30' may be bonded, friction welded, or otherwise permanently coupled along mating transition zone surfaces which may include annular butt joints, male/female connections (as depicted), or other suitable arrangements as desired. Typically, the tube lumen 34 passes substantially unrestricted in cross-sectional area through the body transition zones 340; however, localized deviations may be desirable to enhance coupling strength, modify body transition zone column strength, or facilitate manufacture. Material and geometry of each section 30' may be selected in accordance with the critical load criteria discussed hereinabove to achieve the respective buckling strengths desired.

It is therefore desired to be secured in the appended claims all such modifications as fall within the true spirit and scope of the invention. Accordingly, what is desired to be secured by Letters Patent is the invention as defined and differentiated in the following claims.

I claim:

1. A nasogastric tube for insertion into a digestive system of a patient via a nasal cavity comprising:
 a flexible tube body configured to provide a first column strength, said tube body comprising:
  a sidewall defining a lumen; and
  a distal end portion;
 a tip coupled to said distal end portion along a transition zone, said tip configured to provide a second column strength, wherein said first column strength is greater than said second column strength so that said tip preferentially buckles before said tube body upon encountering body structure during insertion of said nasogastric tube to provide a lumen seeking function; and
 an aperture transecting at least one of said sidewall and said tip, said aperture being in fluid communication with said lumen.

2. The invention according to claim 1 wherein said tip comprises a member selected from the group consisting of cylindrical, frustoconical, tapered, bulbous, pleated, necked, solid, hollow, symmetric and asymmetric members and combinations thereof.

3. The invention according to claim 1 wherein said tip includes an end selected from the group consisting of radiused, truncated and spherical ends and combinations thereof.

4. The invention according to claim 1 wherein at least one of said first column strength and said second column strength varies respectively as a function of position along said tube body and said tip.

5. The invention according to claim 1 wherein said tip comprises at least two adjacent tip members, each member configured to provide a respective column strength and coupled to an adjacent member along a tip transition zone.

6. The invention according to claim 5 wherein said coupling of adjacent tip members comprises a male/female connection.

7. The invention according to claim 1 wherein said coupling of said tip to said body distal end portion comprises a male/female connection.

8. The invention according to claim 1 wherein said coupling of said tip to said body distal end portion comprises an inseparable assembly.

9. The invention according to claim 1 wherein said nasogastric tube further includes a reinforcement member disposed along said tip.

10. The invention according to claim 9 wherein said reinforcement member comprises a coiled wire.

11. The invention according to claim 9 wherein said reinforcement member is anchored in said sidewall.

12. The invention according to claim 1 wherein said nasogastric tube has a smoothly contoured external configuration along said transition zone.

13. The invention according to claim 1 wherein said tip is formed integrally with said body distal end portion.

14. The invention according to claim 1 wherein said tube body has a minimum external diameter of about 6 Fr.

15. The invention according to claim 1 wherein said nasogastric tube further includes a radiopaque marker.

16. The invention according to claim 15 wherein said radiopaque marker is disposed at least in said tip.

17. The invention according to claim 1 wherein said lumen is transected by a septum, along at least a portion thereof, said lumen being thereby divided into multiple lumens.

18. The invention according to claim 1 wherein said tube body further comprises at least two adjacent tube body sections, each section configured to provide a respective column strength and coupled to an adjacent section along a body transition zone.

19. The invention according to claim 18 wherein said coupling of adjacent sections comprises a male/female connection.

20. The invention according to claim 19 wherein said lumen passes through said male/female connection.

21. A method for providing fluidic communication with a digestive system of a patient comprising the steps of:

1) providing a nasogastric tube comprising:
   a flexible tube body configured to provide a first column strength, said tube body comprising:
      a sidewall defining a lumen; and
      a distal end portion;
   a tip coupled to said distal end portion along a transition zone, said tip configured to provide a second column strength, wherein said first column strength is greater than said second column strength so that said tip preferentially buckles before said tube body upon encountering body structure during insertion of said nasogastric tube to provide a lumen seeking function; and
   an aperture transecting at least one of said sidewall and said tip, said aperture being in fluid communication with said lumen;

2) inserting said tip into a nostril of the patient; and 3) passively steering said tip into the digestive system by:
   a) advancing said nasogastric tube until said tip buckles upon encountering body structure;
   b) manipulating said nasogastric tube to bypass said body structure; and
   c) repeating substeps a) and b) until said aperture is disposed in a desired location in the digestive system.

22. The invention according to claim 21 wherein said tube manipulating substep includes a motion from the group consisting of advancing, retracting, dithering, and twisting motions and combinations thereof.

23. A tip for coupling to a nasogastric tube body having a first column strength for insertion into a digestive system of a patient via a nasal cavity, said tip comprising:
   a flexible member configured to provide a second column strength less than said first column strength so that said flexible member preferentially buckles before said tube body upon encountering body structure during insertion to provide a lumen seeking function.

* * * * *